United States Patent [19]

Schlicht et al.

[11] 4,315,826
[45] Feb. 16, 1982

[54] REACTION PRODUCTS OF CARBON DISULFIDE WITH THIOMOLYBDENUM DERIVATIVES OF ALKENYLSUCCINIMIDES AND LUBRICANTS CONTAINING SAME

[75] Inventors: Raymond C. Schlicht; Stephen A. Levine, both of Fishkill; Harry Chafetz, Poughkeepsie, all of N.Y.

[73] Assignee: Texaco Inc., White Plains, N.Y.

[21] Appl. No.: 179,611

[22] Filed: Aug. 19, 1980

[51] Int. Cl.³ ............................................... C10N 1/54
[52] U.S. Cl. ................................ 252/46.4; 252/47.5; 252/49.7; 260/128; 260/429 R
[58] Field of Search .................... 252/46.4, 47.5, 49.7; 260/128, 429 R

[56] References Cited

U.S. PATENT DOCUMENTS

| | | | |
|---|---|---|---|
| 3,223,625 | 12/1965 | Cyphers et al. | 252/46.4 X |
| 3,252,910 | 5/1966 | Oberright | 252/46.4 X |
| 3,281,355 | 10/1966 | Cyphers et al. | 252/46.4 X |
| 3,356,702 | 12/1967 | Farmer et al. | 252/42.7 X |
| 3,400,140 | 9/1968 | Rowan et al. | 252/49.7 X |
| 3,509,051 | 4/1970 | Farmer et al. | 252/46.4 X |
| 4,263,152 | 4/1981 | King et al. | 252/46.4 |
| 4,265,773 | 5/1981 | de Vries et al. | 252/46.4 |
| 4,272,387 | 6/1981 | King et al. | 252/46.4 |

*Primary Examiner*—Andrew Metz
*Attorney, Agent, or Firm*—Carl G. Ries; Robert A. Kulason; Henry W. Archer

[57] ABSTRACT

Disclosed are multipurpose lubricant additives which are prepared by reaction of carbon disulfide with thiomolybdenum derivatives of polyalkenylsuccinimides having basic nitrogen functions. The subject additives function as dispersants possessing excellent anti-frictional properties and impart anti-wear and anti-oxidant properties to a lubricant.

8 Claims, No Drawings

REACTION PRODUCTS OF CARBON DISULFIDE WITH THIOMOLYBDENUM DERIVATIVES OF ALKENYLSUCCINIMIDES AND LUBRICANTS CONTAINING SAME

BACKGROUND OF THE INVENTION

1. Field of the Invention

This invention relates to the preparation and use of reaction products of carbon disulfide with thiomolybdenum derivatives of a polyalkenylsuccinimide of a polyamine. The compositions of this invention are dispersants, anti-oxidants and friction-reducing agents for lubricant compositions.

2. Statement of The Prior Art

Using urethanes or carbamates in lubricating compositions is known. There are also numerous patents on the use of molybdenum derivatives in lubricants. Accordingly, this background disclosure is restricted to those which are believed most relevant.

A pertinent patent is U.S. Pat. No. 3,096,285 which discloses as anti-oxidants urethanes of the formula:

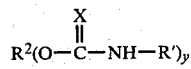

where $R^2$ is a saturated aliphatic radical, y is 1 to 8; $R'$ is a monovalent hydrocarbon radical and X is oxygen or sulfur.

U.S. Pat. No. 2,161,615 is pertinent for describing antiwear agents of the formula:

wherein R and $R'$ are H or alkyl, alicyclic or aryl except that $R'$ cannot be H.

U.S. Pat. No. 2,187,742 is relevant for disclosing that urethanes such as alkyl urethanes lower the coefficient of friction of oils.

Very basic is U.S. Pat. No. 3,356,702 which claims a compound of the general formula:

$$(R_2N-CS-S)_2Mo_2O_mS_n$$

wherein $m+n=4$; m is 2.35 to 3; n is 1.65 to 1 and R is a hydrocarbyl group having 1 to 24 carbon atoms such that the compound $R_2NH$ reacts with $CS_2$ to form a dithiocarbamate.

U.S. Pat. No. 3,400,140 also relates to molybdenum compounds of interest.

As will be seen hereinafter, none of these disclose, hint or suggest in any manner whatsoever applicants' novel, unique and unobvious process which results in novel compounds with very useful properties.

The present invention differs from the prior art in that a thiomolybdenum derivative of an alkenylsuccinimide of a di- or poly-amine is first formed by reaction of hydrogen sulfide with an oxymolybdenum derivative of the alkenylsuccinimide, and the thiomolybdenum derivative is next treated with carbon disulfide to generate the thiocarbonyl species indicated in the general structure shown below:

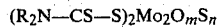

wherein $v=0.5$ to 3, w is such that $v+w=0.5$ to 3, $x=0.8$ to 5, $y=1$ to 3, and z ranges from 0.5 to 5; R = a functionality bearing an alkenylsuccinyl di- or polyamine group having 15 to 300 carbon atoms, and $R'$ can be hydrogen, an alkyl group of 1 to 20 carbon atoms, or an alkenylsuccinyl amine or polyamine group which can be the same as or different from R. Preferably, x ranges from 0.8 to 1.

Although it may be theorized that molybdenum dithiocarbamate moieties may be present in the product, we do not exclude the possible presence of thiourea, ammonium dithiocarbamates, Mo: amine complexes, and ammonium or molybdenum monothiocarbamates, or mixtures of any or all of the above, since the actual composition of the complex products of the reaction cannot be readily ascertained. Both single compounds and mixtures are contemplated as being within the scope of this invention.

SUMMARY OF THE INVENTION

The preparation of the reaction products used in a lubricating composition according to the invention is relatively uncomplicated and can be economically conducted.

The reaction is facilitated by the use of a solvent for the reactants which is inert to the reactants and to the reaction product. A broad range of inert aromatic and aliphatic solvents is suitable for this purpose including benzene, toluene, pentene, hexane, cyclohexane and mixtures of these.

The reaction is broadly conducted at at a temperature in the range of room temperature to 200° C. In practice it is convenient to conduct the reaction at about 35° C. up to the reflux temperature of the solvent or solvent mixture employed for the reaction.

Thus, the process of this invention comprises dissolving a thiomolybdenum derivative of an alkenylsuccinimide in an inert hydrocarbon solvent; adding to the resulting solution a molar charge ratio of about 0.5:1 to 5:1 of $CS_2$ to molybdenum, preferably about 1:1 to 2:1, agitating while raising the temperature from ambient to 40° C. over about 1 to 10 hours; refluxing under an inert atmosphere and azeotroping the water of reaction at a temperature range of about 70° to 200° C. followed by cooling, filtering, and, solvent removal to recover the product.

The starting thiomolybdenum derivative of an alkenylsuccinimide can be prepared by reacting a molybdenum acid or molybdenum oxide (hydrate or otherwise, the oxide in contact with water) with a polybutenylsuccinimide such as the polybutenylsuccinimide of triethylene tetramine.

The preparation of the subject starting compounds is disclosed in greater detail, and claimed in co-pending application Ser. No. 159,040, filed June 13, 1980.

The invention is illustrated in non-limiting fashion by the following examples.

EXAMPLE 1

A 63.5 g. (0.009 g at. of Mo) quantity of a dithiomolybdenum derivative of an polybutenylsuccinimide of triethylene tetramine prepared from a polybutene having a molecular weight of around 1200 was dissolved in 100 ml. cyclohexane. Then 0.82 g. (0.168 mole) of carbon disulfide was added. The mixture was stirred for ½ hour at room temperature and for 1 hour at 40° C. before being heated to reflux under $N_2$. Water was removed by azeotropic distillation over 1 hour at 90° C. (max.). The mixture was cooled, filtered, and stripped of solvent up to 150° C. at 10 mm. The product was polish-filtered at 100°–120°, and gave the following analyses:

% Mo=1.4 and % S=1.86. The S:Mo atomic ratio calculated from these analyses=3.72:1 (vs. 4:1 calculated from the equation).

EXAMPLE 2

This preparation was similar to that of Example I, except that 335 g. (0.05 g. at Mo) of the dithiomolybdenum derivative of the polybutenylsuccinimide used in Ex. 1, 300 ml. cyclohexane, and only 3.04 g. (0.04 mole) of carbon disulfide were employed. The yield was 236 g. The analyses were: % Mo=1.30 and % S=1.28. The S:Mo atomic ratio=2.95:1 (vs. 3.7:1 calculated).

TABLE I

| Ex. No. | Test Oil Formulation[1] Mo Additive Wt. %(% Mo) | Copper Strip Corr. Test 300°/3 Hrs. | 4-Ball Test Wear, mm | 4-Ball Test Frict. Coeff. | Bench III Test % Vis. Increase at 72 Hours | Bench VC Test | Bench L-38 Test mg,BWL | Small Engine Friction Test % Frict. Reduction |
|---|---|---|---|---|---|---|---|---|
| None | — | 1A | 0.41 | 0.095 | Too viscous to measure | 2.0 | 26.6 | 0 ± 2 |
| 2 | 5.90 (0.08) | 1A | 0.33 | 0.073 | 90 | 5.5 | 42.3 | — |
| 3 | 5.55 (0.08) | 1A | — | — | 108 | — | 12.6 | 10.0 |

[1]The test oils were 10W-40 grade oils also containing a succinimide dispersant, a zinc dialkyl dithiophosphate, an overbased calcium sulfonate, an aromatic secondary amine, an ashless inhibitor, a VI improver, a pour point depressant, and an anti-foam agent.

EXAMPLE 3

The preparation is similar to Ex. 1 except that 284.4 g (0.04 g. at. Mo) of the dithiomolybdenum derivative of the polybutenylsuccinimide used in Ex. 1, 300 ml cyclohexane, and 3.04 g (0.04 moles) of carbon disulfide were employed. The yield was 286 g. The analyses were: % Mo=1.44 and % S=1.43. The S:Mo atomic ratio=2.98:1.

The products of the above examples were blended into automotive oil compositions and tested by various tests. Of these, the Bench VC Test measures turbidity, the lower the turbidity values indicated below the better dispersancy. This test is carried out by mixing together exact volumes of the test oil, a synthetic blowby, and a mineral oil diluent in a test bottle. The bottle is then placed on a rocker and rocked for four hours at 280° F. After heating, the sample is diluted with more mineral oil, cooled to room temperature, and the sample's turbidity is measured with a Lumetron turbidimeter equipped with a 700 millimicron filter. Synthetic blowby is a hydrocarbon fraction which has been oxidized under specific conditions. This material emulates the oxidized compounds which find their way past the piston rings and into the crankcase of an internal combustion engine.

The Bench L-38 Test simulates, in a journal bearing rig, the engine test environment of Federal Method No. 791a, Method 3405.1, and provides a method for studying the copper-lead bearing corrosion characteristics of crankcase oils. The copper strip test is based on ASTM Method D-130 and involves immersing a polished copper strip in a given quantity of neat oils and oils containing the additive under test and heating for a temperature and time characteristic of the material being tested. At the end of this period the copper strip is removed, washed and compared with the ASTM Copper Strip Corrosion Standards.

The third test employed was the Four Ball Wear Test described in U.S. Pat. No. 3,384,588 which measures the amount of wear a lubricating oil permits under engine test conditions with and without additives to be tested. The greater amount of wear, the poorer the ability of the test oil composition to prevent such wear. This wear is measured in terms of the wear scar diameter. This test was run here for 2 hours at 600 rpm/200° F./40 kg load. The friction coefficient was measured at the end of the test when the anti-friction film is fully developed.

The Small Engine Friction Test is a single cylinder engine test which measures the frictional characteristics of an oil. The values given in Table I are based on the torque required to motor an engine containing the oil under test. The results of this test have been found to correlate with field experience using a large fleet of cars under varied on-the-road driving conditions as the percentage change in torque correlates with a percent change in fuel economy.

As shown in Table 1, the exemplary preparations gave better results than the reference oil in oxidation, wear, and friction tests and were about equivalent in dispersancy and corrosivity. The large reduction in friction in the Small Engine Friction Test afforded by the oil employing Example 3 demonstrates the efficacy of the subject additives.

Lubricating compositions according to the present invention contain at least one of the products thereof in an amount ranging from about 0.1 to 15.0 percent; preferably between 0.5 and 10.0 percent by weight and especially at least 1.0 percent by weight so as to provide at least 0.01–0.20 weight percent of molybdenum metal. These compositions can also contain a combination of other well known additives in an amount sufficient to achieve each additive's function.

Lubricating compositions according to this invention comprise a major amount of any of the well-known types of oils of lubricating viscosity as suitable base oils. They include hydrocarbon or mineral lubricating oils of naphthenic, paraffinic and mixed naphthenic and paraffinic types. Such oils may be refined by any of the conventional methods such as solvent refining and acid refining. Synthetic hydrocarbon oils of the alkylene polymer type or those derived from coal and shale may also be employed. Alkylene oxide polymers and their derivatives such as the propylene oxide polymers and their ethers and esters in which the terminal hydroxyl groups have been modified are also suitable. Synthetic oils of the dicarboxylic acid ester type including dibutyl adipate, di-2-ethyl-hexyl sebacate, di-n-hexyl fumaric polymer, dilauryl acetate and the like may be used. Alkyl benzene types of synthetic oils such as tetradecylbenzene, etc., are also included.

It is to be understood that the examples presented herein are intended to be merely illustrative of the invention and not as limiting it in any manner; nor is the invention to be limited by any theory regarding its operability. The scope of the invention, therefor, is to be determined solely by the appended claims.

What is claimed is:

1. A composition of the formula:

$$MoS_vO_w(RR'N)_x(CS_y)_z$$

wherein v ranges from 0.5 to 3, w is a number such that v+w ranges from 0.5 to 3, x ranges from 0.8 to 5, y ranges from 1 to 3, and z ranges from 0.5 to 5, R is an alkenylsuccinyl di- or polyamine group having 15 to 300 carbon atoms, and R' is hydrogen, an alkyl group of 1 to 20 carbon atoms, an alkenylsuccinyl amine or an alkenylsuccinyl polyamine group which can be the same as or different from R.

2. The composition of claim 1, wherein R is an alkenylsuccinyl polyamine group in which the alkenyl moiety is a polybutenyl group having about 100 carbon atoms.

3. A composition of claim 1, wherein x ranges from 0.8 to 1.

4. A lubricant composition comprising a major amount of an oil of lubricating viscosity and an effective friction-reducing amount of a composition of claim 1.

5. A process for forming a composition having friction reducing, anti-wear and anti-oxidant properties comprising reacting $CS_2$ with a composition of the formula:

$$MoS_aO_bH_c(RR'N)_x$$

wherein R is an alkenylsuccinyl di- or polyamine group having from 15 to 300 carbon atoms, a=0.5 to 3, b=2.5-0, c=0-3, x=0.8-5; R' is hydrogen, an alkyl group of 1 to 20 carbon atoms, an alkenylsuccinyl amine or an alkenylsuccinyl group which can be the same as or different from R; using a molar charge ratio of $CS_2$ to molybdenum of about 0.5:1 to 5:1, removing the water of reaction which forms and recovering a composition according to claim 1.

6. The process of claim 5, wherein an inert reaction solvent is used to remove the water of reaction by azeotropic distillation.

7. The process of claim 5, wherein the product is recovered by filtration and by distillation to remove said solvent.

8. The process of claim 5, conducted with a molar charge ratio of $CS_2$ to molybdenum of about 1:1 to 2:1.

* * * * *